US009034004B2

(12) United States Patent
Pansky (10) Patent No.: US 9,034,004 B2
(45) Date of Patent: May 19, 2015

(54) DEVICE FOR TRAVERSING VESSEL OCCLUSIONS AND METHOD OF USE

(75) Inventor: Amir Pansky, Atlit (IL)

(73) Assignee: Medinol Ltd., Tel Aviv (IE)

( * ) Notice: Subject to any disclaimer, the term of this patent is extended or adjusted under 35 U.S.C. 154(b) by 275 days.

(21) Appl. No.: 13/022,710

(22) Filed: Feb. 8, 2011

(65) Prior Publication Data

US 2011/0196384 A1   Aug. 11, 2011

Related U.S. Application Data

(60) Provisional application No. 61/302,669, filed on Feb. 9, 2010.

(51) Int. Cl.
| | | |
|---|---|---|
| *A61B 17/22* | (2006.01) | |
| *A61M 25/01* | (2006.01) | |
| *A61B 17/92* | (2006.01) | |

(52) U.S. Cl.
CPC ...... *A61M 25/0116* (2013.01); *A61B 17/22012* (2013.01); *A61B 2017/22014* (2013.01); *A61B 2017/22015* (2013.01); *A61B 2017/22094* (2013.01); *A61B 2017/925* (2013.01); *A61B 2017/928* (2013.01)

(58) Field of Classification Search
USPC .................. 606/37, 38, 40, 49, 159, 169, 170
See application file for complete search history.

(56) References Cited

U.S. PATENT DOCUMENTS

| 5,234,451 | A | | 8/1993 | Osypka | |
|---|---|---|---|---|---|
| 5,626,593 | A | * | 5/1997 | Imran | ............................ 606/159 |
| 2005/0119606 | A1 | * | 6/2005 | Nita | ................................ 604/22 |
| 2009/0292296 | A1 | * | 11/2009 | Pansky et al. | .................. 606/127 |

FOREIGN PATENT DOCUMENTS

| DE | 40 36 570 A1 | 5/1992 |
|---|---|---|
| EP | 0 443 256 A1 | 8/1991 |
| WO | WO 96/08196 A1 | 3/1996 |
| WO | WO 97/19644 A1 | 6/1997 |
| WO | WO 2009/141810 A2 | 11/2009 |

OTHER PUBLICATIONS

International Search Report and Written Opinion from corresponding PCT Application No. PCT/IB2011/000401 dated Jul. 6, 2011, 16 pages.

* cited by examiner

*Primary Examiner* — Thomas McEvoy
(74) *Attorney, Agent, or Firm* — Cadwalader Wickersham & Taft LLP (57) ABSTRACT

An apparatus, system and method for re-canalization or opening a passage through an occlusion in a blood vessel is provided. The apparatus and method, which are appropriate for both cardiovascular as well as peripheral vessels, use a pulling member and a spring element, for example a compression spring, to oscillate a vibratable member, and the system of the invention includes the apparatus and a control unit to permit the frequency or amplitude of oscillation of the vibratable member to be adjusted. Also provided is a method for oscillating a vibratable member using a pulling member and a spring element. The apparatus and system are useful not only for penetrating a total or partial occlusion, but also to improve deliverability of a catheter through a partially occluded vessel or a tortuous vessel.

20 Claims, 4 Drawing Sheets

DEVICE FOR TRAVERSING VESSEL OCCLUSIONS AND METHOD OF USE

FIELD OF THE INVENTION

The invention is directed to an energy efficient apparatus and method of using that apparatus for penetrating a total occlusion of a blood vessel during percutaneous coronary intervention ("PCI") or improving deliverability of a percutaneous transluminal angioplasty (PTA) catheter through a partial occlusion of a blood vessel. In particular, the apparatus provides energy transfer to the distal tip of the PCI device via a pulling force, to penetrate the occlusion with minimal energy loss. The apparatus is also applicable to percutaneous intervention procedures in peripheral arteries.

BACKGROUND OF THE INVENTION

Medical science has long sought effective treatments for disease conditions involving stenosis (narrowing or obstruction) of the lumen of an artery. This condition, known generally as an occlusion, occurs in patients suffering from atherosclerosis, which is characterized by an accumulation of fibrous, fatty or calcified tissue in the arteries, otherwise known as atheromata or plaques. An occlusion may be partial or total; it may be soft and pliable or hard and calcified. Occlusions can arise at a great variety of sites in the arterial system including the aorta, the coronary and carotid arteries, and peripheral arteries. An occlusion can result in hypertension, ischemia, angina, myocardial infarction, stroke and even death.

Minimally invasive procedures are the preferred treatment of arterial occlusions. In these procedures, a catheter—a long, highly flexible tubular device—is introduced into a major artery through a small arterial puncture made in the groin, upper arm, upper leg, or neck. The catheter is advanced and steered into the site of the stenosis. A great variety of devices have been developed for treating the stenosed artery, and these devices are placed at the distal end of the catheter and delivered thereby. Example procedures include percutaneous transluminal coronary angioplasty (PTCA), directional coronary atherectomy (DCA), and stenting.

In a total occlusion, a passageway must first be opened through the occlusion to allow the balloon/stent catheter to be placed in the target stenosed segment of the vessel. As occlusion morphology is complicated and varies from patient to patient, common methods and devices for opening these occlusions have had limited success and require long procedures with potentially adverse effects on the patient. Such adverse effects include perforation of blood vessel wall, high radiation dose or damage to kidneys due to extensive use of angiographic contrast material.

Stenoses, or occlusions, are made of a variety of materials—from softer fatty substances such as cholesterol, to tougher fibrous material, to hard calcified material. Generally the ends of the occlusion—the proximal and distal caps—comprise the harder calcified material. The harder materials are more difficult to penetrate, requiring a significant amount of energy, the softer materials require less energy. Therefore, opening an occlusion requires transfer of relatively extensive energy to the distal end of a catheter or guide wire, especially when calcification is present.

Some available methods for opening total occlusions are radio-frequency ablative energy (as used in the system sold by Intralumenal Therapeutics as Safecross™), vibrational energy of about 20 kHz and small amplitudes (as used in the system sold by FlowCardia Inc. as Crosser™), dedicated stiff guide wire which pushes a passage through the occlusion (as developed by Asahi Intec Co. and distributed as Confianza 9 g/Conquest and Miracle 12 g guide wires) and mechanical vibration elements working at high frequency (FlowCardia Inc.'s Crosser™). The latter means for opening occlusions suffer from significant energy loss between the energy source at the proximal end of the catheter and the driller located at the distal end of the catheter, as well as limited working life due to material fatigue. For example, with an ultrasound catheter, the ultrasonic energy usually originates from an ultrasound transducer at the proximal end of the catheter and is then transmitted to the distal head of the catheter as a sinusoidal wave, causing the distal head to vibrate and either ablate or disrupt the target occlusion. To reach treatment sites, such catheters must be rather long—about 90-150 cm or more—and therefore a large amount of energy must initially be transmitted to reach the distal end. At the same time, to be flexible enough to course through highly tortuous vessels, the catheter must be reasonably thin. The long length and narrow diameter combine to make wire breakage a common problem due to the stress and wear from the high energy pulses. Guide wires stiff enough to penetrate hard occlusions have the disadvantage that their inflexibility and straight tips make navigating through tortuous vessels difficult and increase the risk of vessel perforation. Rigid materials that are sufficiently flexible to accommodate the highly tortuous vessels have the problem of buckling, due to the proximal location of the pushing source. Buckling results in energy loss by transfer to transverse forces and friction against the lumen housing the rigid material. All such devices provide limited success rate ranging from 40-70%.

Occlusions comprise a variety of materials of different density and hardness. Therefore, the nature of the energy used in a re-canalization device should suit the specific occlusion and the penetration should be controlled to prevent perforation of the artery walls or damage to healthy tissue. Additionally, because the energy originates at the proximal end of the catheter it must be able to reach the distal end of the device near the occlusion at a level sufficient to effect penetration of the occlusion without damaging the conductive wires and without sacrificing flexibility of the device. As previously described, current devices suffer either from an insufficient amount of energy transferred to the distal end of the device or a mismatch between the type of energy delivered and the type of occlusion, sometimes resulting in too much force being applied and thereby increasing the risk of damage, or even perforation, of the lumen wall. Accordingly, there is a need for a system or apparatus that can transfer adequate energy to the re-canalization device.

In endolumenal devices designed for penetrating vessel occlusions, mechanical movement, i.e., oscillation, of the member that contacts the occlusion is usually generated by placing an energy source at the proximal end of the device and transferring the energy to the distal end of the device by mechanical means. For example, one prior art device (i.e., FlowCardia Inc.'s Crosser™) uses a rigid Nitinol wire. The rigidity of the wire permits an axial force initiated at the proximal end of the wire to be transmitted to the distal end of the wire, by pushing the wire. However, such energy transfer mechanisms suffer from significant, yet unpredictable (i.e., variable), energy loss due to energy transfer to the housing tube (e.g., catheter lumen). This is a particular problem when the rigid wire bends to conform to the anatomy of the blood vessel. Energy loss of rigid wires are due mainly to two mechanisms: (1) Moment of inertia, which may be illustrated by bending a rigid body. The force imposed to bend the rigid wire is transferred to friction when the rigid wire is housed within a catheter lumen. (2) Buckling of the wire, a situation that causes the axial force to be shifted to transverse forces and results in increased friction forces within the housing lumen. Further, if the axial force is increased to compensate for the energy losses, the buckling is exacerbated, making axial oscillation, and in particular controllable axial oscillation, even more difficult to achieve.

An important engineering phenomenon is the buckling of slender beams upon load. The critical force required to buckle a slender beam (including, for example, a rigid wire) is given by Equation 1:

$$F_c = \frac{\pi^2 EI}{(KL)^2}, \tag{1}$$

where $F_c$ is maximum force the rigid wire can support without buckling, L is the length of the rigid wire, and K is a numeric constant which depends on the way the rigid wire is supported at its ends. For example, if both ends are pinned (i.e., free to rotate), then K=1. If one end is pinned and the other end is fixed, then K=0.7. If a straight wire that is held at its distal end is pushed at its proximal end by a force exceeding the critical buckling force $F_c$, the rigid wire will buckle laterally, and will not transmit the pushing force ahead.

A rigid wire winding within a catheter lumen—in particular a catheter that courses through a tortuous blood vessel—will be bent. Even without pulling or pushing such a rigid wire, there are forces exerted upon the rigid wire to keep it bent. Friction created by the bent wire against the lumenal surface of the catheter causes the rigid wire to be pinned at some point. If the friction at the pinned point is larger than the buckling threshold, a buckling will occur and adversely affect the pushability of the wire. The resistance that a rigid wire meets at a vessel occlusion works the same way as a pinned point due to friction at a bend. A rigid wire in a tube such as a catheter will move only if the pushing force is larger than the friction force or resistance acting upon the rigid wire. If the length of the straight portion of the rigid wire preceding the point of resistance is long enough, however, the rigid wire will buckle before the pushing force becomes large enough to overcome the friction. This explains why it is difficult to transmit a force to one end of a winding rigid wire by pushing from the opposite end, because the rigid wire is expected to buckle.

Therefore, there is a need in the art for an apparatus for penetrating vessel occlusions that is capable of delivering efficient energy in a controlled and safe manner to open vessel occlusions, and to improve the deliverability of catheters carrying such devices through blood vessels. There also is a need for a system that both transfers adequate energy and can adjust the amount of energy transmitted to the penetrating end of the device based on the hardness of the occlusion.

SUMMARY OF THE INVENTION

It is an object of the invention to provide an improved apparatus for penetrating a vessel occlusion and/or traversing a partial occlusion, where the apparatus has a vibratable member that is made to vibrate in an improved manner, namely, by more efficient energy transfer from the external energy source to the distal part of the catheter. The increased efficiency derives from the pulling wire-spring combination of the apparatus. In particular, the apparatus generates a vibration force that oscillates the vibratable member by a pulling force rather than pushing or combined pulling-pushing force. The apparatus of the invention is less sensitive to unpredictable geometry such as the sometimes tortuous curvature of blood vessels than PCI devices that use pushing forces.

It is a further object of the invention to provide a system comprising an apparatus with a pulling force for penetrating a vessel occlusion that is capable of adjusting the frequency or amplitude of vibration to accommodate the hardness of the occlusion or stretching of the pulling member.

The invention is directed to an apparatus for re-canalization of a total or partial occlusion in a body lumen, such as a blood vessel. In particular, the apparatus of the invention comprises a spring element, a pulling member, a vibratable member, all housed in a catheter, and an external vibrational energy source operably connected to the pulling member. At the distal tip of the apparatus is a vibratable member, which may be, for example, a cap—similar a catheter cap, or a cap shaped to increase mechanical impact and improve penetration. The vibratable member oscillates in response to the pulling force of the pulling member and the return force from the spring element. The oscillation or vibration of the vibratable member can effect penetration of the occlusion. Specifically, the vibrational energy source is adapted to repeatedly pull and release the pulling member so as to vibrate the vibratable member via the spring element. The pulling member is capable of simultaneously compressing the spring element in the proximal direction and therefore transferring energy to the vibratable member. The spring element is capable of converting the stored energy to kinetic energy locally (upon release of the pulling member tension), thereby moving the vibratable member in the distal direction. The acceleration of the kinetic energy carries the expansion of the spring element to extend the distal end of the spring element beyond the no load (resting) position, thereby pushing the vibratable member further distally. In a blood vessel having an occlusion, the kinetic energy is transferred from the vibratable member to impact the occlusion. The vibratable member, located at the distal tip of the catheter, is thereby made oscillate at a frequency and amplitude sufficient to penetrate an occlusion in a body lumen. The catheter may be a conventional interventional medical catheter having a lumen to accommodate the pulling member and preferably also a lumen to accommodate a guide wire as well as other elements such as for steering, motion measurement element, to infuse contrast material, or to remove occlusion debris from the drilling area.

The vibrational energy source is external of the catheter, but is operably connected to the pulling member, which moves freely relative to the catheter. The vibrational energy source may be any energy source that is capable of generating at least one vibratory energy pulse by pulling and releasing. The vibrational energy source may be, for example, a motor, a shaker, a piezoelectric motor or an actuator. The vibrational energy source pulls the pulling member to generate potential energy in the spring element. The potential energy converts to kinetic energy when tension in the pulling member is released, the load on the spring is lifted and the spring element expands naturally, thereby locally transferring mechanical energy to the vibratable member, which may be either attached to or part of the distal end of the spring element, pushing the vibratable member toward the occlusion. The process is repeated at a frequency and amplitude that enables the vibratable member to drill through the occlusion. The amount of energy can be adjusted by choosing an appropriate "spring" element having an internal spring factor (k). The force is further adjusted by setting externally the pulling member amplitude. The amount of power (energy over time) as well as the mechanical impact can be controlled by the oscillation frequency.

The apparatus may additionally comprise a device that secures the catheter relative to the blood vessel to improve the delivery vibration forces to the occlusion. The apparatus may still further comprise a steering device to assist navigation through an occlusion, especially for use in cases where there are numerous bifurcations near the target occlusion. The catheter may be compatible for use with additional external or internal components that assist visualization of the apparatus or device, and/or to remove drilling debris, for example by suction.

The system of the invention comprises the apparatus of the invention and a control unit adapted for controlling the vibrational energy source, and thereby adjust the frequency and/or amplitude of vibration of the vibratable member. Preferably, the control unit may adjust the vibrational energy source to generate a vibration force suitable for the occlusion morphology and hardness, the vibration force having at least one frequency and at least one amplitude. Suitable vibration force may be achieved by adjusting the frequency, e.g., from several Hz to several hundred Hz, and/or adjusting the pulling amplitude, so that the penetration force of the vibration is minimized and is appropriate for the occlusion morphology and hardness. The at least one frequency and at least one amplitude generated by the vibrational energy source may be adjusted via the control unit to suit the occlusion being treated. Optionally, the system of the invention further comprises an operator interface unit and a sensor to assist the operator in controlling the frequency and amplitude of vibration of the vibratable member based on feedback from the sensor regarding hardness of the occlusion and/or $\Delta y$ of the spring member.

It is believed that by providing the minimal force necessary to penetrate an occlusion, safety of the recanalization procedure is increased and potential damage to the body lumen, e.g., an artery, is reduced compared to recanalization devices in the art. Accordingly, the frequency and/or amplitude of vibration of the vibratable member may be changed manually by the physician operator to adjust for the hardness of the particular occlusion being treated, based on the operator's skill and experience. Alternatively, the frequency and amplitude of vibration may be adjusted automatically or manually based on measurements of the hardness of the occlusion. Where the hardness of the occlusion is to be measured, the apparatus of the invention may further comprise a sensor or strain gauge. In such embodiments, the control unit may further comprise a processor, or an operator interface unit comprising a processor may be used, the processor being capable of analyzing input from the sensor or strain gauge to calculate tissue hardness or amplitude of vibration and the operator interface unit being capable of providing the calculations in a user-readable form. Either the control unit or operator interface unit may comprise one or more adjustor means for the operator to adjust manually the frequency and/or amplitude of the pulling force generated by the vibrational energy source. Optionally, the operator interface unit may further comprise a display unit for displaying information regarding occlusion hardness.

The system may further include a tension control mechanism to compensate for variations in the path of the pulling member in curved or tortuous lumens. The tension control mechanism may adjust the length of the pulling member or the amplitude that the pulling member is pulled.

The invention further encompasses a method of oscillating the vibratable member, a method of using the apparatus or system for recanalization of an occluded body lumen, such as a blood vessel, and a method of controlling the force of vibration in the apparatus. The result is a versatile and efficient energy delivery apparatus, system and method for penetrating a total occlusion and/or improving deliverability of the catheter through partially occluded body lumens.

DESCRIPTION OF DRAWINGS

FIGS. 1A-E illustrate one way an embodiment of the apparatus of invention may work during one pulling cycle.

FIG. 2 is a series of schematic diagrams depicting components of a tissue sensor according to the invention.

DETAILED DESCRIPTION OF THE INVENTION

In order to overcome the mechanical energy loss limitations of prior art devices, the apparatus of the invention uses a distal spring-like element that can store potential energy. The potential energy is loaded and released to kinetic energy at desired frequency by pulling and releasing a flexible pulling member. As used herein, the term "flexible" is intended to mean capable of flexing laterally without any inertia moment, e.g., to accommodate tortuous vessels, but not longitudinally—e.g., the pulling member should be minimally stretchable or extensible lengthwise. By "releasing the pulling member" is meant that the tension—generated in the pulling member by pulling the pulling member—is released. In parallel to the release of tension in the pulling wire, the potential energy of the spring element is released to kinetic energy. The stored energy of the spring element is released to the surrounding tissue or occlusion via a vibratable member which impacts the occlusion. An advantage of the pulling member feature of the invention is that the force will not significantly diminish in strength from the proximal end of the apparatus where the energy is generated to the distal end of the apparatus, where the vibratable member impacts the occlusion. Another major advantage of the invention is that the force is fully controlled by the user (amplitude and frequency), allowing the user to match the force to the occlusion and keep the procedure safe.

In contrast to the energy lost when transmitting energy from the proximal to distal end of a device, as is typical of prior art devices, energy loss is minimized in the instant invention by use of a spring element and pulling member combination. Various amplitude-force combinations can be achieved by appropriate choice of spring element placed at the distal end of the catheter.

To overcome the limitations of the prior art—in particular the loss of mechanical energy, the apparatus of the invention comprises a spring-like element at its distal end to transmit force locally. The spring element is capable of being charged—i.e., being compressed to generate potential energy—by pulling a pulling member. The potential energy is converted to kinetic energy upon release of the tension in the pulling member. Thus, the apparatus of the invention comprising a pulling and releasing process becomes more efficient than pushing a stiff wire, even when the path of the pulling member deviates from a straight path, for example when the catheter flexes. The more efficient energy transfer feature of the present invention provides improved penetration of partially or totally occluded vessels as well as improved deliverability of PTA catheters.

The apparatus, system and method of the invention provide an improved device and method of oscillating a vibratable member for re-canalization of a total occlusion in a blood vessel. The apparatus of the invention may also be applicable to clearing occlusions from other body lumens. Specifically, the apparatus of the invention comprises a catheter having a proximal end and a distal end; a spring element having a proximal end and a distal end, said proximal end of said spring element being affixed to said distal end of said catheter; a pulling member located within said catheter, said pulling member having a proximal end and a distal end, said distal end of said pulling member affixed to a distal component; a vibratable member; and a vibrational energy source operably connected to said proximal end of said pulling member, wherein said vibrational energy source is adapted to generate at least one oscillation in said vibratable member via said pulling member and said spring element.

The apparatus of the invention provides therapeutic vibration in a vibratable member at the distal end of the catheter. The force for generating therapeutic vibration of the vibratable member is provided by the vibrational energy source, which is capable of pulling the pulling member at a distance (x), to generate a tension (T), and then releasing the tension. The pulling member is functionally connected at its distal end, via a distal component, to a spring element. A return force is provided by the spring element, having a spring constant (k), such that the tension in the pulling member may be defined as $T=kx$. The repeated combination of pulling and releasing of the pulling member generates oscillations in a vibratable member at a frequency and amplitude to sufficiently penetrate and clear a vessel occlusion.

The pulling member preferably is a flexible string. Any high tensile polymer would be suitable material for a pulling member. Non-limiting examples of suitable materials include carbon, DSM Dyneema® or Dyneema Purity® (available from DSM, Heerlen, Netherlands), or other suitable polymers, such as a polyethylene or a polyester.

The spring element may be, for example, a compression spring, a helical spring (e.g., a wire in the shape of a helix), a leaf-spring, a bellows, a compressible polymer, an elastic membrane, a coated spring, or similar member suitable for storing potential energy upon compression and releasing kinetic energy when the compression load is lifted. The compression and expansion of the spring element may thereby be used to vibrate a vibratable member at a frequency and amplitude sufficient to penetrate a vessel occlusion.

The distal component to which the pulling member is attached may be the vibratable member or the distal end of the spring element.

The vibratable member is the portion of the apparatus that impacts the occlusion. The vibratable member may be, for example, a cap affixed to the distal end of the spring element, the distal end of an active bellows, or the outer surface of an elastic membrane, e.g., where the elastic membrane is a spring element. Vibration of the vibratable member is effected by the pulling and releasing of the pulling member via a spring element, directly or indirectly, depending on whether the spring element is designed to impact the occlusion. Where the spring element is of a design that its distal portion is the structure that impacts the occlusion, e.g., the outer surface of an elastic membrane or the distal end of an active bellows, the vibratable member is that distal portion of the spring element.

The vibrational energy source may be, for example, a vibrational shaker, an actuator, a solenoid, a standard motor, or any similar energy source having a reciprocating member that can pull and release the pulling member. By "release" is meant releasing the tension in the pulling member, the tension being generated by pulling the pulling member. The vibrational energy source is located external of the catheter. The vibrational energy source may mechanically pull the pulling member, the pulling member may cause the spring element to compress, and the vibratable member thereby may be made to move proximally. Then, after tension in the pulling member is released, causing the spring element to expand, the vibratable member may be made to move distally.

Preferably the catheter has one or more lumens for the pulling member(s) and a lumen for a guide wire. The catheter may also include various lumens for other features, such as a steering wire or other mechanism, contrast materials for visualization, IVUS (intra-vascular ultrasound), elements for measuring distal motion amplitude and force, removal of debris from the occlusion, etc.

The system of the invention comprises the apparatus of the invention and a control unit for controlling the frequency and/or amplitude of the pulling (and thus indirectly also the frequency and/or amplitude of vibration of the vibrating member). The amplitude of pulling should not exceed the elastic limit of the spring element, and preferably the frequency of pulling should not exceed the natural frequency of the spring. The operator may adjust the vibration by manually adjusting the frequency and/or amplitude of vibration directly through the control unit. The control unit may comprise adjustor means, such as knobs, dials, buttons levers and the like, digitally or in analog, similar to a rheostat or potentiometer, that permit adjustment of the amplitude or frequency that the vibrational energy source pulls the pulling member. The particular frequency or amplitude at any given time may be controlled by adjusting the vibrational energy input via the control unit, which may be adjusted manually by the operator directly via the control unit.

The invention further provides a method of oscillating a vibratable member in an occlusion penetrating device (the apparatus) and a method of treating a vessel occlusion using the apparatus, for example to recanalize an occlusion. Also provided is a method of controlling the force of vibration.

The method of oscillating a vibratable member comprises providing a pulling member, a spring element and a vibratable member, wherein said vibratable member is functionally attached to a distal end of said spring element; pulling said pulling member to generate a load that compresses said distal end of spring element toward a proximal end of said spring element; releasing said load generated by said pulling member, thereby permitting said spring element to expand; repeating said pulling and releasing steps to effect said oscillation of said vibratable member. By "functionally attached" is meant that the pulling member is attached to a distal component, which permits the load generated by pulling the pulling member (T=kx) to be transferred to the spring element to charge the spring element. The distal component may be, for example, the distal end of the spring element or the vibratable member attached to the distal end of the spring element.

The method of treating a vessel occlusion may comprise introducing the apparatus of the invention into said vessel; positioning said distal end of said catheter in contact with said occlusion; generating a series of pulling forces from said vibrational energy source upon said pulling member to oscillate said vibratable member and penetrate said occlusion. The method may further include advancing said apparatus through said occlusion as said vibratable member penetrates said occlusion.

Occlusions, in particular vascular occlusions, tend to have non-uniform density and hardness. Penetrating harder parts of an occlusion requires a relatively larger force than what is necessary for softer parts of the occlusion. The system of the invention comprises a control unit that is capable of adjusting the force applied against the occlusion by adjusting frequency or by adjusting the amplitude of oscillation of the vibratable member at the behest of the physician or automatically.

The minimal force necessary to recanalize a path through an occlusion is realized by the combination of frequency and amplitude of vibration. Increasing the amplitude of vibration or increasing the frequency of vibration will increase the force. Decreasing the amplitude or frequency of vibration will decrease the force. Determining the appropriate force for a given occlusion may be done "by feel" by the physician operator, based on the physician's experience and diagnostic skill. The operator may adjust the vibration to provide an appropriate force to penetrate an occlusion, by manually adjusting the frequency and/or amplitude of vibration directly through the control unit. Alternatively, the apparatus of the invention may further comprise a sensor (e.g., a tissue sensor) designed to measure directly or indirectly the hardness or stiffness of the biological matter forming the occlusion, and the amplitude and/or frequency of vibration of the vibratable member may be adjusted based on feedback from the sensor. In such embodiments, feedback from the sensor to a processor in either the control unit or user input-output device (also referred to herein as an operator interface unit) may allow the frequency and/or amplitude of vibration may be adjusted automatically by the control unit or manually by the physician operator based on operator-readable output from the user input-output device, optionally further comprising a display screen. In embodiments in which the operator adjusts the vibrational energy source, the control unit or operator interface unit may comprise adjustor means, such as knobs, dials, buttons levers and the like that permit adjustment of the amplitude or frequency of the pulling force generated by the vibrational energy source, digitally or in analog, similar to a rheostat or potentiometer.

In embodiments where the apparatus of the invention comprises a tissue sensor, the sensor may be located at the distal end of the catheter to directly measure the resistance the occlusion impact element encounters against the occlusion. Occlusion hardness also may be determined by measuring how much the spring element expands. In one mode of operation for directly measuring expansion of the spring element a magnetic sensor may be located in the catheter, for example attached to the internal catheter wall or changes in the amount of expansion or rate of deceleration upon impact with the occlusion may indirectly measure hardness or stiffness of the occlusion. The expected amplitude of oscillation of the vibratable member (i.e., vibration force amplitude) may set by the operator, and if the spring element expands less than the set amount, the calculated difference provides a measure of how much more pulling force is required to achieve the correct amplitude of oscillation to penetrate the occlusion. In any mode of operation, the sensor may provide feedback to a processor that generates a readable output for the operator who can manually adjust the energy pulse input and subsequent pulling force through a control unit. Alternatively, the sensor may provide feedback directly to the control unit that can be made to adjust the pulling force input automatically.

The sensor may be, for example, a strain gauge sensor, a piezoresistor, a microstrain sensor, or a magnetic sensor. A strain gauge is a device used to measure deformation (strain) of an object. The most common type of strain gauge consists of an insulating flexible backing which supports a metallic foil pattern. The gauge is attached to the object by a suitable adhesive, such as cyanoacrylate. As the object is deformed, the foil is deformed, causing its electrical resistance to change. This resistance change, usually measured using a Wheatstone bridge, is related to the strain by the quantity known as a gauge factor. Commercial example of such a strain gauge that may be useful in the present invention is the Vishay 015DJ strain gauge (Vishay Intertechnology, Inc., Malvern, Pa., U.S.A.). A piezoresistor is a resistor made from a piezoresistive material having a sensitivity proportional to the piezoresistive gauge factor of the piezoresistor, which is defined by the relative change in resistance with strain. Silicon is a common material with which to form sensors comprising piezoresistors. Such piezoresistor sensors may comprise, for example, four 6-10 µm by 30-50 µm piezoresistors implanted in a high aspect-ratio cross-shape flexible element having a 525 µm high silicon mesa, as described in Beccai, L. et al., "Design and fabrication of a hybrid silicon three-axial force sensor for biomechanical applications," *Sensors and Actuators A: Physical*, Vol. 120, Issue 2, pp. 370-382, May 17, 2005. Piezoresistors are also described in U.S. Pat. Nos. 4,419,598 and 6,441,716, which are incorporated herein by reference; WO 2005/106417 describes strain sensors based on piezoresistor nanowires. Magnetoelastic sensors are low cost, miniature sensors with no moving parts, having other properties expected useful for biological applications. Magnetoelastic sensors are described in U.S. Pat. No. 7,062,981, which is incorporated herein by reference. Commercial examples of such magnetoelastic sensors that may be useful in the present invention are DVRT Microminiature Displacement Sensors (MicroStrain, Inc., Burlington, Vt., U.S.A.).

Embodiments of the invention are described in detail below with reference to the drawings. The drawings, which are schematic and not necessarily to scale, are provided to depict particular aspects of the embodiments and are not intended to limit the scope of the invention.

In the particular embodiment illustrated in FIGS. 1A-E, the spring element 20 is shown as a helical compression spring. The pulling member 10 is attached, at its distal end, to a distal component 30, in this case a cap, which is attached to the distal end of the spring element 20 (compression spring) and serves as the vibratable member. The spring element 20 is attached at its proximal end to the distal end of the catheter 40. A compression spring is designed to provide resistance to compressive forces. In accordance with the invention, the pulling member 10 is used to compress the spring element 20 (compression spring) at a tension (T), where T=kx, (k) is the spring constant and (x) is the spring deflection (also referred to herein as "compression distance")—ideally, the distance the pulling member 10 is pulled. Upon release of the tension on the pulling member 10, the spring element 20 (compression spring) naturally expands and preferably if no resistance exists the spring element 20 (compression spring) expands further approximately a distance (y) before returning to its unloaded position (0). In cases where the spring element meets resistance, such as an occlusion, the spring will expand to the point it hits the occlusion and may not reach the expansion position attainable in the absence of resistance. In such cases Δy will be less than Δy$_x$, where y$_x$ is the natural expansion for a spring element compressed by x (deflection=x). The optimal spring constant (k) for such a compression spring in accordance with the invention is between about 0.1-10 Newton per mm.

Preferably, where the form of the compression spring is a wire or strip, it has closed ends or closed and ground ends.

Figure 1:
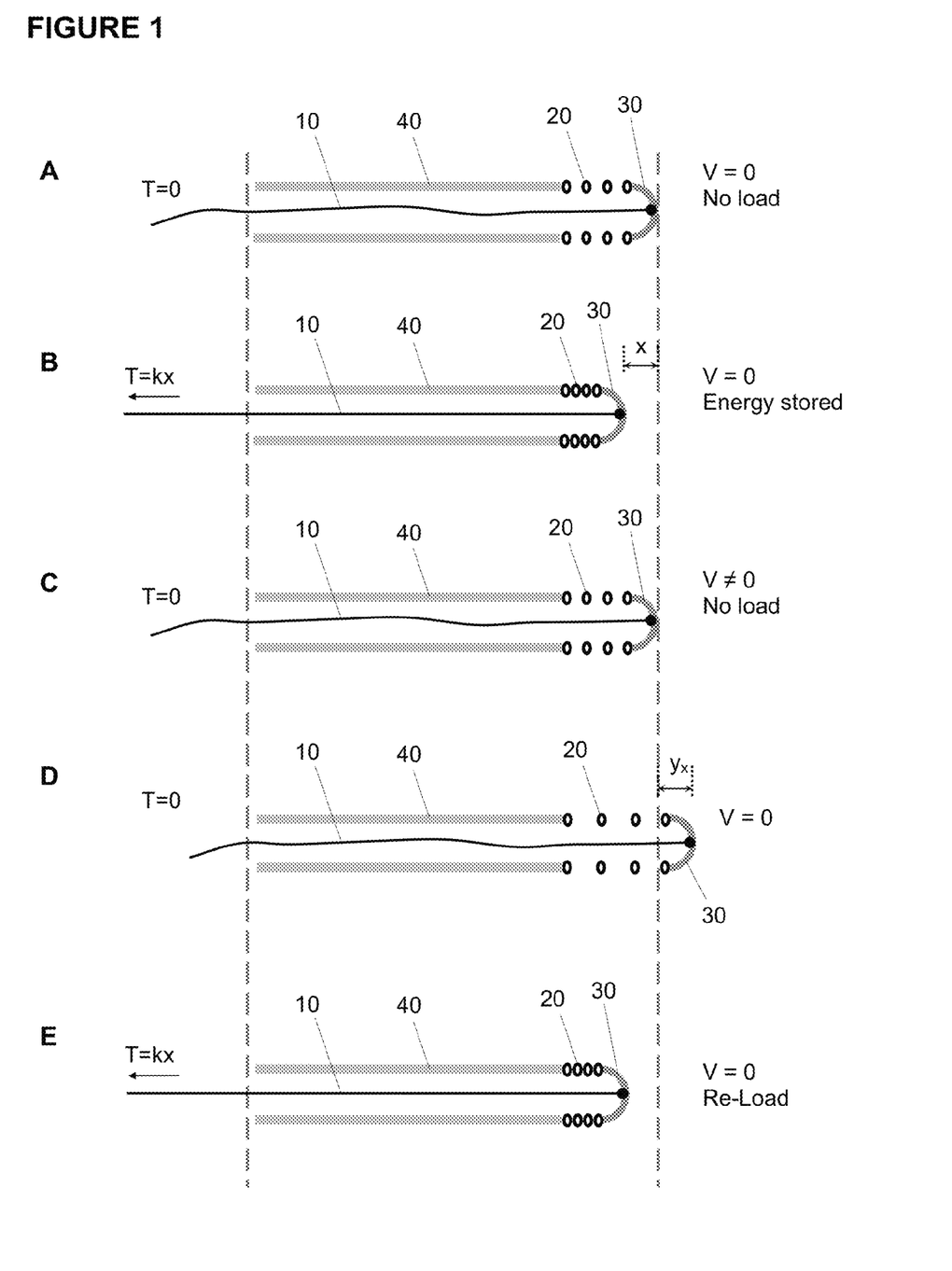
FIG. 1A depicts an apparatus with no tension placed on it.
FIG. 1B depicts the apparatus with tension in the pulling member, and a compressed spring with load (stored energy). Stored energy is equal to spring constant (k) multiplied by compression amplitude (x).
FIG. 1C depicts the apparatus with no tension in the pulling member released, and kinetic energy releasing from the compression spring.
FIG. 1D depicts the apparatus with no tension in the pulling member, and the compression spring at maximum expansion ($y_x$) for the compression amplitude (x).
FIG. 1E depicts the apparatus with tension on the pulling member again.

FIGS. 1A-E illustrate more particularly in transverse section through the catheter the status of an embodiment of the apparatus of the invention comprising a compression spring at different points in time during one pulling cycle. In the context of this drawing, "one pulling cycle" means one pull and release of the pulling member. As shown in FIG. 1B, when tension (T) is applied to the pulling member 10, the spring element 20 is compressed, thereby storing energy. FIG. 1C illustrates the apparatus at some stage after the pulling member 10 has been released, dropping the tension in the pulling member 10 to zero (T=0). Upon release of the pulling member 10 by the vibrational energy source (not shown), the spring element 20 expands in the axial direction. Expansion of the spring element 20 moves the vibratable member—in this embodiment a cap—distally at a rate greater than 0 (V>0). The rate of mechanical movement (V, velocity) of the cap at the time illustrated in FIG. 1C, where kinetic energy is maximal as the spring element 20 is midway between peak compression and peak expansion for the given applied tension (i.e., equivalent to its resting position), may be expressed as $V=2\pi \sin(2\pi f \cdot t)$, where A is the compression amplitude, f is the frequency, and t is time. This velocity of course excludes forces exerted in the proximal direction by an occlusion. As shown in FIG. 1D, in the absence of external resistance such as a vessel occlusion, the spring element 20 will continue to expand beyond its resting position a distance (y$_x$), which may be approximately equal to (x), where the velocity reaches zero again (V=0) and then naturally compress—providing a return force—towards its resting position (deflection=0). In use, at this point, the vibrational energy source will again pull the pulling member 10 a distance (x), as illustrated at the peak tension (T=kx) in FIG. 1E.

The repeated pulling and releasing of the pulling member results in oscillation of the vibratable member, which is attached to the distal end of the spring element. The amplitude of oscillation of the vibratable member may be controlled by the distance the pulling member is pulled. The frequency of oscillation will be a function of the rate of pulling the pulling member and the spring constant. The frequency of the pulling/releasing generated by the vibrational energy source preferably is lower than the natural frequency of the spring.

The embodiment illustrated in FIGS. 1A-E shows the pulling member attached to a cap, which serves as the vibratable member of the apparatus. In this embodiment the oscillating cap will be the element of the apparatus that, in use, comes into contact with the vessel occlusion and serves as the part of the apparatus that penetrates and drills through the occlusion. The cap may comprise metal, hard plastic, or other suitable materials. The cap may have any of a number of suitable shapes or contours to optimize the balance between impact force and safety.

Other spring elements may operate in the same manner in accordance with the invention. Alternatively, where the amplitude of the vibration is desired to be minimal and the frequency and force higher, the distal component to which pulling member may be attached is the proximal end of the spring element, the spring element may be an extension helical spring, which has a cap at its distal end which serves as the vibratable member that impacts the occlusion.

In another embodiment, the spring element is a bellows. As used herein, the bellows is essentially a sealed element which has a return force (spring constant) built into it and may be, for example, a sealed coated spring or corrugated tube comprising a compression spring. The bellows may have an open design or a closed design. By "closed design" for a bellows is meant that one end of the bellows is closed, as a cup; by "open design" for a bellows is meant that both ends of the bellows are open, as a tube. For the closed design, the closed end would be located at the distal end. Thus, where the bellows is a closed design, the bellows is operably connected at its distal closed end to the pulling member. The structures of these bellows may be designed so that they may be contracted upon load from the pulling member and returned (expanded) by the internal spring force upon removal of the external load. Bellows useful in the present invention are available from, for example, MS Bellows, 5322 McFadden Ave, Huntington Beach, Calif. 92649. The terms "bellows" and "spring bellows" are used interchangeably herein. Alternatively, the ordinarily skilled artisan can make a distal bellows by covering a spring with a polymer or embedding a spring in a polymer, such that the polymer membrane is extensible in the longitudinal (axial) direction. Preferably the polymer material has a lower durometer (shore) than the material making up the outer walls of the catheter.

In this embodiment the distal component, to which the pulling member is attached, may be the distal end of a closed bellows or a vibratable member, such as a cap, attached to the distal end of the bellows. In this arrangement, similar to the compression spring, when the vibrational energy source exerts a tension on the pulling member, the pulling member causes the bellows to compress, so that the distal end of the bellows is deflected by distance (x). When the vibrational energy source releases the tension on the pulling member, the bellows expands, and the distal end of the bellows is returned to its unloaded position (deflection 0), and preferably moves distally beyond (0) to a deflection of approximately (y) distally, before returning to the unloaded position (0).

According to this embodiment, the bellows are intended to compress upon load from the pulling member and expand upon removal of the load. The repeated loading and unloading of the bellows results in an oscillation of the distal end of the bellows to which is attached the vibratable member.

In another embodiment, the spring element may be an elastic membrane. In this embodiment, the elastic membrane also may function as a distal element and vibratable member. The elastic membrane may comprise a biologically compatible elastomer such as polyurethane, elastic silicon, or other biologically compatible elastic materials known in the art. The elastic membrane at the distal end of the catheter comprises the most distal aspect of the apparatus so as to permit contact with the target surface, e.g., the surface of an occlusion, to effect penetration of the occlusion.

Pulling the pulling member moves the elastic membrane in the proximal direction, release of the pulling member causes the elastic membrane to retract in the distal direction, due to its innate elasticity. Thus, in use, the pulling and releasing of the pulling member causes an oscillation of the elastic membrane so that the elastic membrane operates as a vibratable member that vibrates at a frequency and amplitude useful for penetrating an occlusion. The distal movement of the elastic membrane would contact the proximal surface of the occlusion being recanalized.

In other embodiments, other spring elements may operate in the same manner in accordance with the invention.

The apparatus and system of the invention are compatible for use with imaging components to assist the operator in determining the location of the distal end of the catheter relative to the target occlusion or vessel walls during operation of the device. Thus, the apparatus or system may further comprise imaging components and an imaging system, for example, IVUS, OCR, Doppler ultrasound or other imaging systems known in the art. The catheter may further comprise one or more lumens for optional components, such as a lumen for visualization or imaging component—for example, IVUS, OCR, Doppler ultrasound, fiber optics, or contrast agents, as well as an auxiliary lumen for housing such useful components as steering components or other therapeutic components. A lumen may be designed to function as a guide wire lumen for insertion of the catheter into the body lumen, and then when the guide wire is not needed, it may be removed and the lumen may be used to deploy a visualization device for use during operation of the apparatus—e.g., penetration and traversal of an occlusion. Alternatively, this lumen can be used for suction of debris away from the drilling area during penetration of the occlusion.

In any one of the embodiments of the invention, the apparatus may optionally include a catheter anchoring element that secures the catheter to the walls of the blood vessel. The catheter anchoring element may be used to stabilize the catheter within the body lumen during operation, so as to prevent substantial movement in response to the vibrational forces and to secure the catheter to the walls of the blood vessel to improve vibration force delivery. The catheter anchoring element may be serviced by an anchoring element lumen. The catheter anchoring element may be, for example, one or more expandable balloons. In such an embodiment, the anchoring element lumen may be an inflation lumen filled with a fluid, preferably a liquid, more preferably a biologically compatible liquid, and used to inflate (expand) the one or more expandable balloons to secure the catheter in the blood vessel. Securing the catheter in this manner will make the vibration forces more effective in treating certain types of occlusions.

Thus, the apparatus of the invention may comprise the following. In one embodiment the apparatus for penetrating a vessel occlusion, comprises: a catheter, having a proximal end and a distal end; a spring element having a proximal end and a distal end, said proximal end of said spring element being affixed to said distal end of said catheter; a pulling member located within said catheter, said pulling member having a proximal end and a distal end, said distal end of said pulling member affixed to a distal component; and a vibratable member. In another embodiment, the apparatus for penetrating a vessel occlusion, comprises a catheter, having a proximal end and a distal end; a spring element having a proximal end and a distal end, said proximal end of said spring element being affixed to said distal end of said catheter; a pulling member located within said catheter, said pulling member having a proximal end and a distal end, said distal end of said pulling member affixed to a distal component; a vibratable member; and a vibrational energy source operably connected to said proximal end of said pulling member, wherein said vibrational energy source is adapted to generate at least one oscillation in said vibratable member via said pulling member and said spring element by pulling said pulling member. In either embodiment, the pulling member may be a flexible string. In one aspect of either embodiment, said distal component is said vibratable member. In another aspect of either embodiment, said distal component is said distal end of said spring element. In another aspect of either embodiment, said vibratable member is a cap, and said cap is affixed to said distal end of said spring element. In one aspect, said spring element is selected from the group consisting of: a compression spring, a helical spring, a leaf spring, a bellows, a compressible polymer, and an elastic membrane. In another aspect, said vibrational energy source is selected from the group consisting of: an engine having a reciprocating member, a shaker, an actuator, and a solenoid. In another embodiment, the apparatus further comprises a catheter anchoring device. In one aspect, said catheter anchoring device is an expandable balloon. In another embodiment, the apparatus further comprises a catheter steering device.

The invention also encompasses a system as follows. A system of the invention, comprises any one of the embodiments of the apparatus of the invention; and a control unit adapted to control said vibrational energy source. In one embodiment of the system of the invention, said oscillation comprises at least one frequency and at least one amplitude, and said at least one frequency and at least one amplitude are independently adjustable via said control unit. In another embodiment, the system further comprises an imaging system, and wherein said catheter further includes a visualization or imaging component lumen. In another embodiment, the system further comprises a sensor, and a processor functionally connected to said sensor and operably connected to said control unit, said processor being capable of analyzing input from said sensor. In one aspect said processor is operably connected to an operator interface unit. In another aspect said operator interface unit comprises a display unit. In one embodiment of the system comprising a sensor, said sensor input comprises information regarding occlusion hardness. In this aspect said sensor may be attached to the vibratable member. In another embodiment of the system comprising a sensor, said sensor input comprises information regarding the amplitude of vibration (achieved amplitude) of said vibratable member. In this aspect said sensor may be a magnetic sensor attached to an interior wall of said catheter. Alternatively, in this aspect said sensor may be a magnetic sensor attached to an interior wall of a sensor lumen of said catheter. In either aspect of this embodiment, said sensor may be operably attached to said vibratable member via a magnetic rod. Alternatively in either aspect of this embodiment, said sensor may be operably attached to said distal end of said spring via a magnetic rod.

The system of the invention may further include a tension control mechanism to compensate for changes in shape of the catheter (i.e., changes in the distance through the catheter that the pulling member must traverse) during operation. For example, if the catheter is routed through a curved or tortuous lumen, the path that the pulling member takes through the catheter lumen changes, for example tending toward the inside of the curve rather than through the middle of the lumen. This can amount to about a 1% or so difference in distance from the vibrational energy source to the distal component of the apparatus, thereby affecting the efficiency of pulling the pulling member to effect oscillation at the vibratable member at the distal end of the catheter. A shorter path may result in decreased tension on the pulling member, and a greater pull amplitude by the vibrational energy source may be required to achieve a constant tension. In order to accommodate changes in the pulling member path and control the pulling member tension, in one embodiment the system may include a tension control mechanism that adjusts the length of the pulling member. In this way, the tension of pulling member may be maintained at the desired constant tension, thereby improving efficiency of the apparatus. The tension control mechanism may adjust the length of the pulling member. In a preferred aspect of this embodiment, the length of the pulling member is adjusted in the region between the catheter body and the motor of the vibrational energy source. In an alternative embodiment, the system may include a tension control mechanism that adjusts the amplitude that the pulling member is pulled.

The invention additionally encompasses a method of oscillating a vibratable member. In one embodiment, the method of oscillating a vibratable member comprises: pulling a pulling member from a proximal end of said pulling member to generate a load that compresses a distal end of a spring member toward a proximal end of said spring member, said pulling member attached at a distal end to said distal end of said spring member, said spring member attached at a proximal end to a distal end of a catheter, said catheter housing said pulling member, wherein said vibratable member is functionally attached to said distal end of said spring element; releasing said load generated by said pulling member, thereby permitting said spring element to expand; repeating said pulling and releasing steps to effect oscillation of said vibration member. In one aspect of the embodiment, said pulling and releasing steps are performed by a vibrational energy source. In aspect of the embodiment, said oscillation has at least one frequency and at least one amplitude, wherein said at least one frequency is controlled by a control unit functionally attached to said vibrational energy source. In another aspect of the embodiment, said oscillation has at least one frequency and at least one amplitude, wherein said at least one amplitude is controlled by a control unit functionally attached to said vibrational energy source. In another embodiment, the method of oscillating a vibratable member comprises: providing a pulling member, a spring element and a vibratable member, wherein said vibratable member is functionally attached to a distal end of said spring element; pulling said pulling member to generate a load that compresses said distal end of spring element toward a proximal end of said spring element; releasing said load generated by said pulling member, thereby permitting said spring element to expand; repeating said pulling and releasing steps to effect said oscillation of said vibratable member.

The invention further encompasses a method of traversing a vessel occlusion. In one embodiment, the method comprises introducing into said vessel an apparatus according to the invention; generating a series of pulling forces from said vibrational energy source upon said pulling member to oscillate said vibratable member. In one embodiment, the method further includes positioning said distal end of said catheter in contact with said occlusion; and oscillating said vibratable member at an amplitude and frequency sufficient to penetrate said occlusion. In one aspect of this embodiment, the method further includes advancing said apparatus through said occlusion as said vibratable member penetrates said occlusion. In another embodiment, the method includes oscillating said vibratable member at an amplitude and frequency sufficient to maneuver said catheter around obstacles in said vessel or through tortuous portions of said vessel.

Figure 2A:
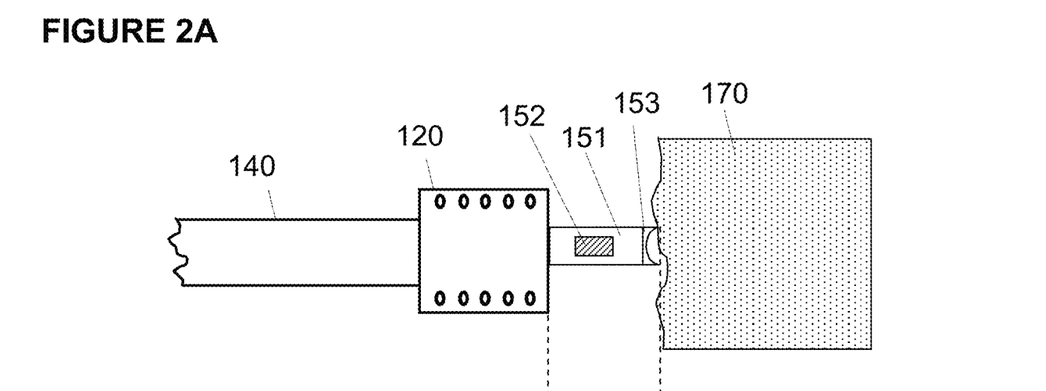
FIGS. 2A-2C illustrate how an embodiment of a tissue sensor attached to a spring member might be used to determine whether the appropriate force is applied to occlusions of differing hardness.
Figure 2B:
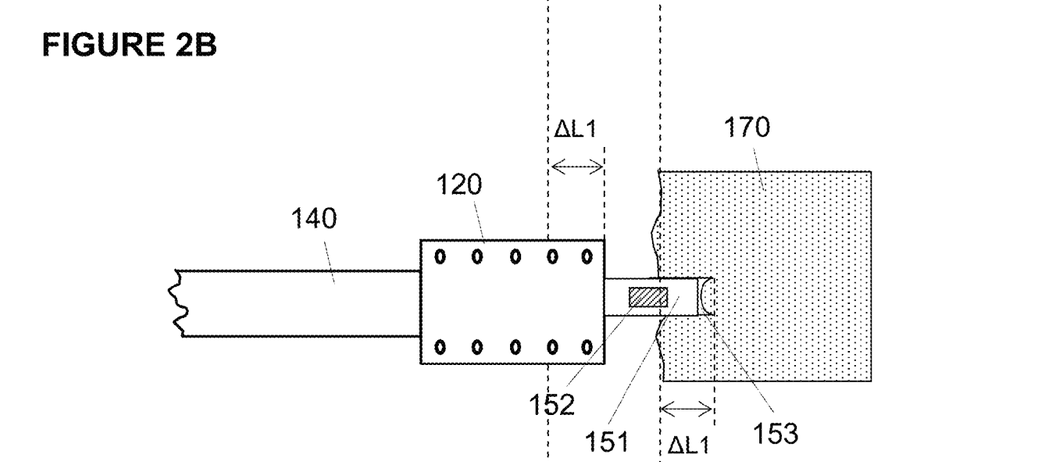
Figure 2C:
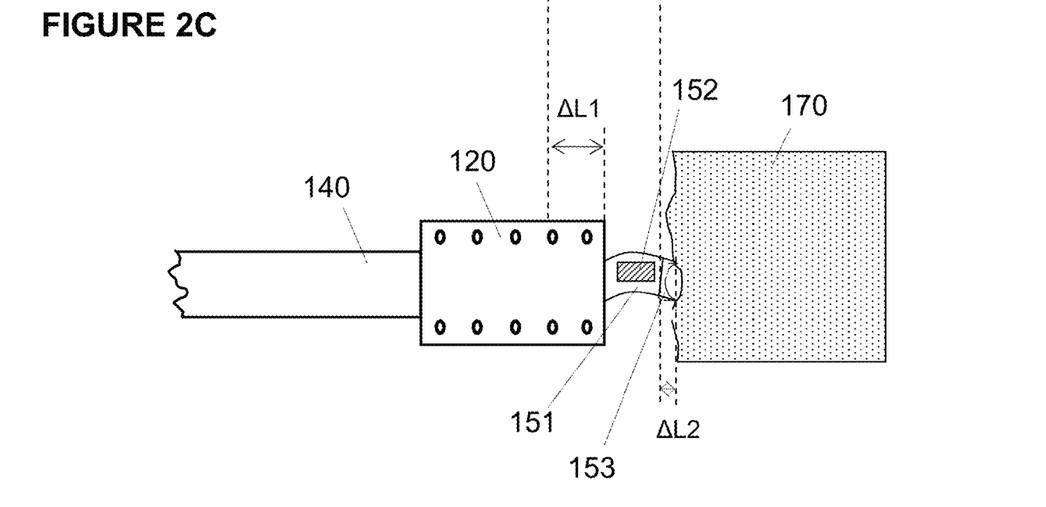
Figure 3:
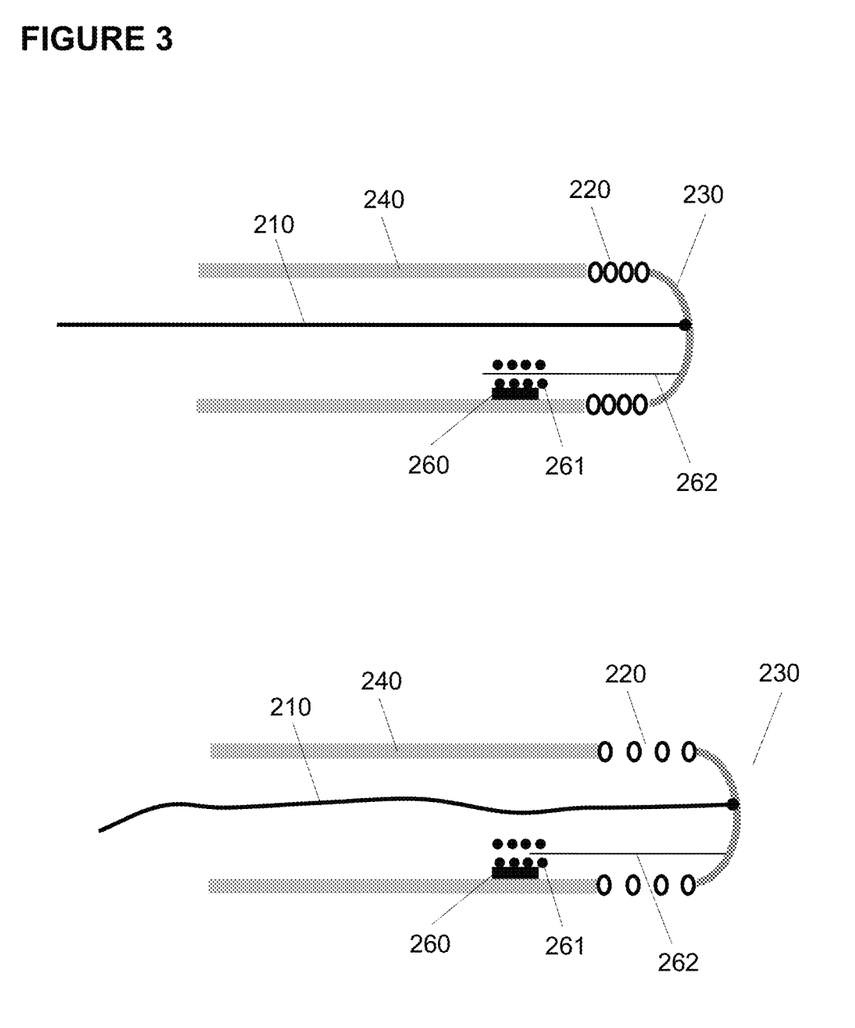
FIG. 3 illustrates schematically how an embodiment of a sensor might be used to measure directly the achieved amplitude of vibration of the vibratable member.

The apparatus of any embodiment of the invention may further comprise a sensor for measuring the hardness of the occlusion to be penetrated. FIGS. 2A-C illustrate aspects of a tissue sensor and its operation with respect to the invention. In particular, FIGS. 2A-C illustrate one way to measure whether desired amplitude is achieved, using a tissue sensor comprising a probe, strain gauge and touch sensor. FIG. 3 illustrates a sensor for directly measuring the amplitude of vibration of the vibratable member.

The system may be set by the operator to achieve desired displacement, or target penetration amplitude ($A_0$). The target amplitude, $A_0$, may not be achieved, however, if the applied force does not match the occlusion hardness, and the achieved amplitude (A) must be determined. The achieved amplitude, A, may be monitored via a sensor in any one of several ways described below or that will become apparent to the person of ordinary skill in the art in view of the examples set forth below. For example, achieved amplitude, A, may be measured directly, for example using a strain gauge or by measuring displacement of the distal end of the spring element 120. In such embodiments, the sensor may comprise a probe 151, strain gauge 152, and touch sensor 153, which, as depicted in FIGS. 2A-2C, measure occlusion hardness separate from stress on the vibratable member. Alternatively, the sensor may comprise a magnetic sensor 260 that may be attached directly to the vibratable member 230, as depicted for example in FIG. 3 to measure the amplitude of vibration of the vibratable member 230. As the apparatus comprises a spring element 220 that is compressed by pulling the pulling member 210 and upon release expands to exceed its resting position to an extension state, penetration amplitude may be determined by measuring the actual extension distance (achieved amplitude, A, affected by resistance generated by the occlusion) and comparing the expected extension distance of the spring element 220.

The force required to penetrate an occlusion may be estimated using Eq. 2:

$$F = ES\left(\frac{\Delta L}{L_0}\right), \quad (2)$$

where F is the force applied to the object, E is Young's Modulus (hardness or stiffness) of the occlusion, S is the original cross-sectional area through which the force is applied (i.e., the cross-sectional area of the probe or sensor), $\Delta L$ is the amount by which the length of the object changes, and $L_0$ is the original length of the object. To define the mechanical properties of the occlusion tissue, so as to adjust the frequency and amplitude for penetration, two parameters should be monitored: force (F) and displacement (L). Of the other parameters of Eq. 2, S—the cross-sectional area of the probe or sensor (which may be a guide wire or other element with known dimensions)—is known, whereas L—the length of occlusion—is unknown. Nevertheless, the force required to penetrate a tissue of unknown hardness may be determined, as illustrated in FIGS. 2A-2C. A catheter 140, a spring member 120 attached to the distal end of the catheter 140, and sensor is provided. The sensor comprises a probe 151, a strain gauge 152, and a touch sensor 153. There are two modes in the working cycle, the measurement mode and the vibration mode. First in the sequence is the measurement, second in the sequence is vibration. In measurement mode, when the touch sensor 153 is placed close to the occlusion 170 and touches it, as shown in FIG. 2A (a contact the physician-operator can feel), the measurement mode is switched on. Measurement mode is a single pulse mode, and the probe may penetrate into the occlusion.

As force (F) is a function of mass (m) and acceleration ($a_{peak}$) an applied force in vibration may be defined as set forth in Eq. 4:

$$F = ma_{peak} = m4\pi^2 \Delta L f^2 \quad (3).$$

Thus, in accordance with Eq. 3, the amount of force to apply is determined by displacement ΔL and frequency f. Fixing ΔL (stroke or amplitude of vibration, equivalent to the movement of the distal end of the spring) at a specific target value, for example, 0.1 mm (a value determined from a safety standpoint), force F may be changed by varying the frequency f. At the starting point, the force pulse is provided at a defined frequency f and amplitude A. FIG. 2B illustrates an applied force that is sufficient to penetrate the occlusion at the full depth ΔL. That the target displacement as been achieved may be confirmed with a magnetic sensor, which may provide signals proportional to bending or strain of the probe. See FIG. 3. In some cases, the pulling member may be made of material that stretches slightly when a critical pulling force is exceeded. Practically, the catheter is unlikely to be completely straight, but rather may be curved or undulating due to the shape of the body lumen, especially in blood vessels. This means that the initial pulling force provided by the vibrational energy source may be absorbed in the pulling member to some extent and cannot be taken at face value for an estimation of occlusion hardness or target amplitude, $A_0$. Moreover, the operator may push the catheter with unknown force, which cannot be controlled or readily measured by the apparatus. In such circumstances, not only the occlusion length but also the actual applied force at the distal end is approximate. Nevertheless, under such conditions, estimation of occlusion tissue mechanical characteristics may be made in relative rather than absolute terms, i.e., values at the distal end can be calibrated from the values at the proximal end. If the initial inputted vibration force is $F_0$ with stroke (amplitude) $\Delta L_0$ at the proximal point, it will reach values $F_1$ and $\Delta L_1$ at the distal point. Thus, if the applied force is sufficient to penetrate into the occlusion tissue 170, the penetration depth will be almost the same as stroke value $\Delta L_1$ or amplitude as shown on FIG. 2B. By contrast, if the applied force is insufficient for full penetration, the probe 151 may bend, as illustrated in FIG. 2C, and the strain gauge sensor 152 may provide a corresponding signal. In this scenario, the applied force may be increased by changing its frequency (frequency-dependent vibration mechanism) or its amplitude (amplitude-dependent vibration mechanism).

A magnetic sensor 260 may be attached to the internal catheter 240 wall or to the internal wall of a sensor lumen within the catheter and be operably connected to the vibratable member 230 via a magnetic rod 262 as illustrated in FIG. 3. The magnetic rod 262 is movable with the oscillation of the vibratable member 230 by pulling and releasing of the pulling member 210. The amplitude of vibration of the vibratable member 230 is thereby measureable by the magnetic sensor 260. Alternatively, the magnetic rod 262 may be connected directly to the distal end of the spring element 220 (embodiment not shown). In either embodiment, the magnetic sensor 260 measures directly the achieved amplitude at the distal end of the catheter 240. The achieved amplitude may be less than the target amplitude due to, for example, the resistance encountered by impacting the occlusion. The magnetic sensor 260 depicted in FIG. 3 is a linear variable differential transformer (LVDT) and shows the magnetic rod 262 moveable within the coils 261 of the LVDT, however other magnetic sensors may also be used for direct measurement of achieved amplitude of vibration in accordance with the invention.

Figure 4:
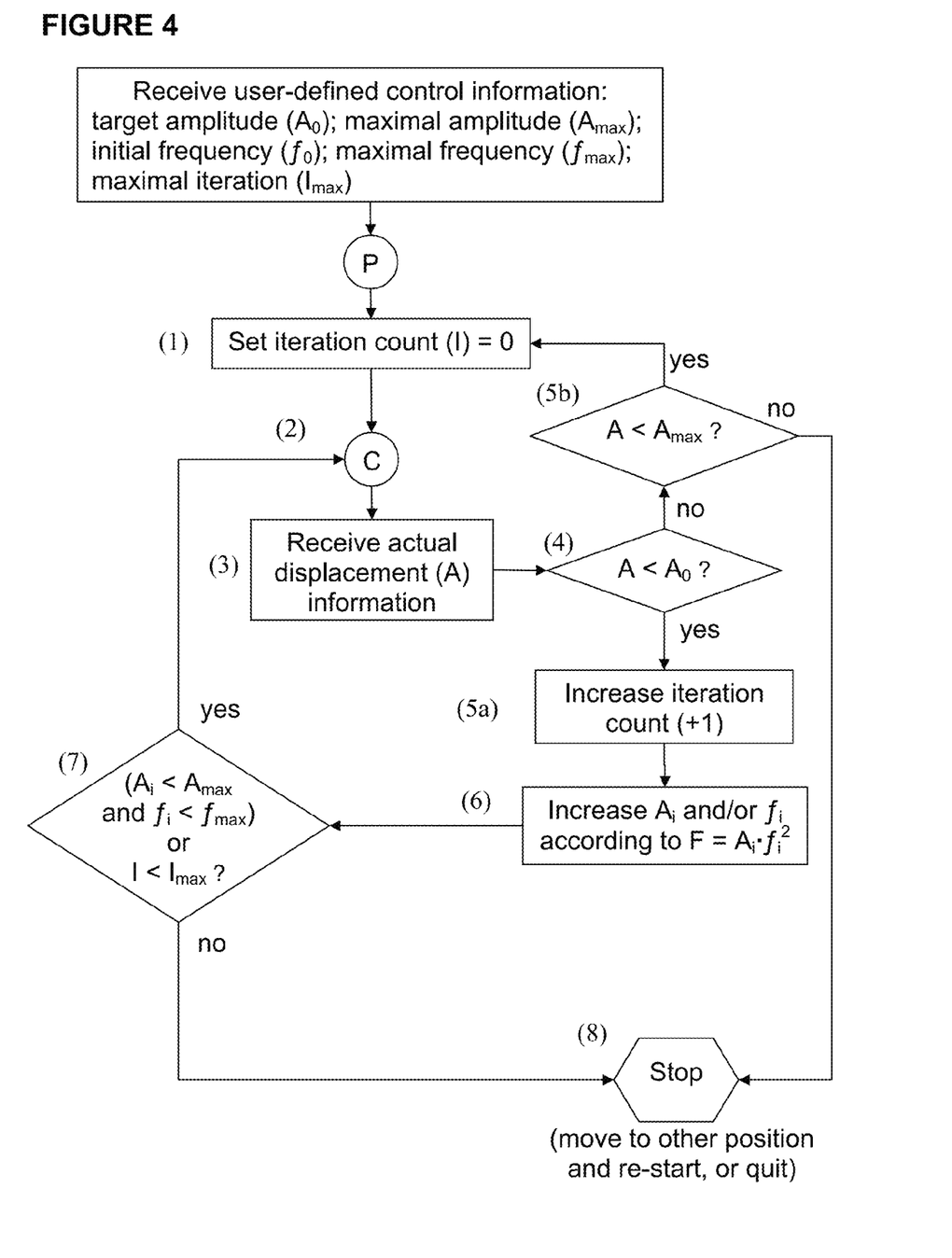
FIG. 4 illustrates one embodiment of a control scheme for adjusting the force of vibration.

The invention encompasses a method of controlling the vibration force. FIG. 4 illustrates one way a control unit might be used in accordance with the invention to monitor penetration amplitude and adjust the amplitude of oscillation if necessary. Control of the frequency and amplitude of vibration is best understood in the context of penetrating an occlusion, such as a vascular occlusion. When the system of the invention is used to penetrate a vessel occlusion, complete penetration may occur over a series of penetration cycles in which frequency and a target amplitude are set prior to initiating vibration in the apparatus, and then adjusted by the control unit throughout the penetration cycle. Each penetration cycle may involve a series of vibration "cycles", in which the effectiveness of the vibration is periodically measured, and the force adjusted as necessary in a manner to maximize both safety and success of penetration. As discussed above, in one mode of operation, the desired penetration amplitude (stroke) may be set at a fixed distance. The control unit of the system of the invention may be used to monitor whether this target penetration amplitude is achieved and to adjust the amplitude and/or frequency of vibration to increase the vibration force accordingly, based on Eq. 4:

$$F = A \cdot f^2 \qquad (4).$$

Thus, in such a mode of operation, at the beginning of a penetration cycle, the apparatus may be placed at a first surface of an occlusion, and series of vibration cycles (C) is initiated wherein the control unit controls the force of vibration in response to information from the sensor by adjusting the frequency and/or amplitude of vibration. Once the first surface is penetrated, the apparatus may be advanced to a new face or surface of the occlusion, and a new penetration cycle may be commenced. In this way, the surface of the occlusion may be penetrated in a step-by-step fashion.

Preferably, a penetration cycle (P) begins after initializing the control unit with control information—values relating to amplitude, frequency and vibration adjustment iterations. The control information may be built into the control unit or may be set by the operator. In the embodiment depicted in FIG. 4, the control unit receives the control information from the operator, who sets the initial (target) displacement or amplitude ($A_0$), a maximal displacement ($A_{max}$)—taking into account safety considerations, an initial frequency ($f_0$)—based on assessment of the plaque density, a maximal frequency ($f_{max}$), and a maximal iteration ($I_{max}$). The target amplitude may be, for example, between about 20 μm and about 200 μm. The maximum amplitude may be determined by the operator, for example, based on the lumen diameter and other factors familiar to the skilled artisan. The initial frequency ($f^0$) and maximum frequency ($f_{max}$) may be determined by the operator based on, for example, the particular occlusion to be penetrated and the physical limits of the apparatus or system being used. The control unit preferably has an iteration counter for counting iterations in which the vibration force is changed. The iteration count (I) is not a measure of the number of vibration cycles (V), rather the iteration count is increased only when frequency and/or amplitude are increased. Thus, a vibration cycle (C) may or may not include an adjustment of frequency and/or amplitude, depending on the achieved amplitude (see below). A maximum iteration value ($I_{max}$) may provide either a safety measure (as it may reflect increase in vibration force, as shown below) or a means for an operator to periodically assess the success of the penetration cycle and make adjustments to the procedure as necessary, or both. The series of vibration cycles (C) in the penetration cycle (P) preferably are continuous until the penetration cycle is stopped either by the control unit or the operator. Thus, as used herein, "beginning" or "initiating" a vibration cycle (C) is meant the point in the series of vibrations after the achieved amplitude is compared to the control information. A vibration cycle (C) may be based on units of time or the number of vibrations. Specifically, a vibration cycle (C) can be a predetermined length of time (e.g., 5 seconds or 10 seconds) or a predetermined number of vibration peaks (frequency×time, e.g., number of times the occlusion impact element contacts the occlusion face).

In accordance with the control scheme embodiment illustrated in FIG. 4, after receiving the control information, the control unit sets the iteration count (I) at zero (Step 1). The vibrational energy source is made to generate a pulling force on the pulling member, and a vibration cycle (C) is begun (Step 2). The pulling force having a working amplitude ($A_i$) is expected to generate a distal displacement beyond the resting position of the spring. Distal displacement, or achieved amplitude (A), is measured, preferably via the sensor, and periodically transmitted to be received by the control unit (Step 3), which compares the achieved amplitude (A) to the target amplitude ($A_0$) (Step 4). If the achieved amplitude (A) is less than target amplitude ($A_0$), then an iteration count (I) is added (Step 5a), i.e., I+1, and the working amplitude ($A_i$) and/or working frequency ($f_i$) increased (Step 6) to increase vibration force, in accordance with Eq. 5:

$$F=A_i f_i^2 \quad (5),$$

where subscript "i" reflects the current iteration count. The force of the oscillated system is proportional to the square of the frequency and amplitude, as shown in Eq. 4 and 5. It is believed that, from a clinical perspective it is better to work at low amplitude, preferably in the range of up to approximately 100 μm (0.1 mm). Thus, to maintain safety of the occlusion penetration procedure, is preferable to increase force by increasing frequency, however the physical structure of the apparatus may impose upper limits on the frequency. So to achieve adequate force for penetration of an occlusion, either frequency or amplitude may be increased up to the maximum values set in the control information. The gain of the amplitude and/or frequency may be increased by about 2% to about 5% each iteration. Thus, for a given total increase in force in a penetration cycle, the number of iteration counts may depend on the percent gain used.

After the vibration force is increased, the iteration count (I) is compared to the maximum iteration value ($I_{max}$), and the working amplitude ($A_i$) and working frequency ($f_i$) are compared to maximum amplitude ($A_{max}$) and maximum frequency ($f_{max}$), respectively (Step 7). If the iteration count (I) is less than the maximum iteration value ($I_{max}$), or if the working amplitude ($A_i$) is less than the maximum amplitude ($A_{max}$) and the working frequency ($f_i$) is less than the maximum frequency ($f_{max}$), the next vibration cycle (C) is initiated (Step 2) at the new working amplitude, new working frequency and new iteration count; the achieved amplitude (A) is again received (Step 3) and compared to the initial (target) displacement ($A_o$) (Step 4), and the cycle continues. However, if after increasing the force, the iteration count (I) is not less than the maximum iteration value ($I_{max}$), and the working amplitude ($A_i$) is not less than the maximum amplitude ($A_{max}$) or the working frequency ($f_i$) is not less than the maximum frequency ($f_{max}$), then the vibration cycle (C) and penetration cycle (P) are stopped (Step 8), and the apparatus may be repositioned within the lumen and a new penetration cycle commenced, or the occlusion penetration is ended.

If, after comparing the measured displacement (achieved amplitude, A) to target amplitude ($A_0$) (Step 4), the achieved amplitude (A) is not less than the target amplitude ($A_0$), then the achieved amplitude (A) is compared to the maximum amplitude ($A_{max}$) (Step 5b). If the achieved amplitude (A) is less than the maximum amplitude ($A_{max}$), the iteration count (I) set to zero (Step 1), and a new vibration cycle is initiated (Step 2) at the same working frequency ($f_i$) and working amplitude ($A_i$), etc. However, if the achieved amplitude (A) is not less than the target amplitude ($A_O$) (Step 4) and also is not less than the maximum amplitude ($A_{max}$) (Step 5b), the vibration cycle (C) and penetration cycle (P) are stopped (Step 8), and the apparatus may be repositioned within the lumen and a new penetration cycle commenced, or the occlusion penetration is ended.

Thus, a method of controlling the frequency and amplitude vibration, and hence the force of vibration, of the apparatus of the invention is provided. In one embodiment, the method for controlling a force of vibration is based on the scheme depicted in FIG. 4. Thus, one method of controlling a force of vibration comprises: a) receiving initial control parameters; b) initiating a vibration iteration cycle comprising at least one pull and release of a pulling member by a vibrational energy source sufficient to vibrate a vibratable member at a vibration force (F), wherein said pulling member is attached to a distal component located at a distal end of a spring element and at a proximal end to said vibration energy source, wherein said spring element is attached at a proximal end to a distal end of a catheter, said catheter houses said pulling member, and said vibratable member is attached to said distal end of said spring element, and wherein said pull and release of said pulling member effects a compression and expansion of said spring element; c) receiving an achieved amplitude value input for said vibration iteration cycle; and d) adjusting said vibration force in accordance with said achieved amplitude value. In one aspect, said receiving initial control parameters includes (i) receiving a target amplitude value input; ii) receiving a maximum amplitude value input; iii) receiving an initial frequency value input; iv) receiving a maximum frequency value input; and v) receiving a maximum iteration value input. In another aspect said initiating includes (i) initializing an iteration count to zero; and (ii) commencing said vibration iteration cycle in said apparatus, wherein said at least one pull and release occurs at an initial frequency and a target amplitude. In yet another aspect said adjusting includes (i) comparing said achieved amplitude value to a target amplitude value and to a maximum amplitude value; (ii) increasing an iteration count by one when said achieved amplitude value is less than said target amplitude value, setting said iteration count to zero when said achieved amplitude value is not less than said target amplitude value, and stopping said vibration iteration cycle when said achieved amplitude value is not less than said target amplitude value and not less than said maximum amplitude value; and (iii) increasing said force of vibration by increasing a frequency gain and/or an amplitude gain by about 2-5% in accordance with the equation $F=A_i \times f_i^2$ to generate a new working frequency ($f_i$) and/or a new working amplitude ($A_i$) if said iteration count is increased by one. In a further aspect, said method includes e) comparing said iteration count to a maximum iteration value, comparing said working amplitude to a maximum amplitude value, and comparing said working frequency to a maximum frequency value; f) initiating a new vibration iteration cycle in said apparatus: if said iteration count is less than said iteration maximum value, or if said working amplitude is less than said maximum amplitude value and said working frequency is less than said maximum frequency value; and g) stopping said vibration iteration cycle: if said iteration count is not less than said iteration maximum value, and if said working amplitude is not less than said maximum amplitude value or said working frequency is not less than said maximum frequency value.

Another method of controlling a force of vibration comprises: a) receiving initial control parameters; b) initiating a vibration iteration cycle comprising at least one pull and release of a pulling member sufficient to vibrate a vibratable member at a vibration force (F); c) receiving an achieved amplitude value input for said vibration iteration cycle; and d) adjusting said vibration force in accordance with said achieved amplitude value. The step of receiving control information may further include: (i) receiving a target amplitude value input; ii) receiving a maximum amplitude value input; iii) receiving an initial frequency value input; iv) receiving a maximum frequency value input; and v) receiving a maximum iteration value input. The step of initiating a vibration cycle may further include: (i) initializing an iteration count to zero; and (ii) commencing said vibration iteration cycle in said apparatus, wherein said at least one pull and release occurs at an initial frequency and a target amplitude. The step of adjusting said vibration force may further include: (i) comparing said achieved amplitude value to a target amplitude value and to a maximum amplitude value; (ii) increasing said iteration count by one when said achieved amplitude value is less than said target amplitude value, setting said iteration count to zero when said achieved amplitude value is not less than said target amplitude value, and stopping said vibration iteration cycle when said achieved amplitude value is not less than said target amplitude value and not less than said maximum amplitude value; and (iii) increasing said force of vibration by increasing a frequency gain and/or an amplitude gain by 2-5% in accordance with the equation $F = A_i \times f_i^2$ to generate a new working frequency ($f_i$) and/or a new working amplitude ($A_i$) if said iteration count is increased by one. This embodiment of the method of controlling a force of vibration may further comprise: e) comparing said iteration count to a maximum iteration value, comparing said working amplitude to a maximum amplitude value, and comparing said working frequency to a maximum frequency value; f) initiating a new vibration iteration cycle in said apparatus: if said iteration count is less than said iteration maximum value, or if said working amplitude is less than said maximum amplitude value and said working frequency is less than said maximum frequency value; and g) stopping said vibration iteration cycle: if said iteration count is not less than said iteration maximum value, and if said working amplitude is not less than said maximum amplitude value or said working frequency is not less than said maximum frequency value.

In another embodiment, the method comprises: a) receiving a target amplitude value input, a maximum amplitude value input, a target frequency value input, a maximum frequency value input, and a maximum iteration count input; b) initializing an iteration count to zero; c) initiating a vibration iteration cycle comprising at least one pull and release of a pulling member sufficient to vibrate a vibratable member for an iteration at a force of vibration (F); d) receiving an achieved amplitude value input for said vibration iteration cycle; e) comparing said achieved amplitude value to said target amplitude value; f) increasing said iteration count by one and increasing said force of vibration by increasing a frequency gain and/or an amplitude gain by 2-5% in accordance with the equation $F = A_i \times f_i^2$ to generate a working frequency ($f_i$) and/or an working amplitude ($A_i$) if said achieved amplitude value is less than said target amplitude value, and then proceeding to step (j); g) comparing said achieved amplitude value to said maximum amplitude value if said achieved amplitude value is not less than said target amplitude value; h) initializing said iteration count to zero if said achieved amplitude value is less than said maximum amplitude value, and recommencing method at step (c); i) proceeding to step (m) if said achieved amplitude value is not less than said maximum amplitude value; j) comparing said iteration count to said maximum iteration count, comparing said working amplitude to said maximum amplitude value and comparing said working frequency to said maximum frequency value; k) recommencing method at step (c): if said iteration count is less than said maximum iteration count, or if said working amplitude is less than said maximum amplitude value and said working frequency is less than said maximum frequency value; l) proceeding to step (m): if said iteration count is not less than said maximum iteration count, and if either said working amplitude is not less than said maximum amplitude value or said working frequency is not less than said maximum frequency value; and m) stopping said vibration iteration cycle.

The above-described embodiment is only exemplary and is not intended to limit the ways in which a control unit might operate. Any number of control schemes for adjusting the frequency and/or amplitude of vibration may be used. Other methods for control unit operation should be within the skill in the art in view of the disclosure herein. For example, a control scheme may include reducing the vibration force by decreasing the working amplitude when the achieved amplitude is not less than the target amplitude and not less than the maximum amplitude for one or more iterations, before stopping the vibration cycle and penetration cycle.

As described above, there are several ways to monitor the achieved amplitude (A). It can be done using a tissue sensor to measure occlusion hardness or degree of occlusion penetration or using a magnetic sensor to measure displacement of the distal end of the spring element. Preferably, the occlusion penetration procedure begins at a minimal force, which is gradually increased according to the hardness of the tissue. A control algorithm also may be used to calculate the force required based on the feedback regarding occlusion hardness.

In view of the method of adjusting a force of vibration, the method of treating a vessel occlusion may further include the step of adjusting the frequency and/or amplitude of vibration via a control unit based on occlusion hardness using an embodiment of the above method of controlling force of vibration. Preferably, where the vibration frequency is adjusted to achieve an appropriate force based on information regarding occlusion hardness or displacement of the distal end of the spring element, the device includes a sensor and the occlusion hardness and spring displacement is determined from information from the sensor. In some embodiments, the adjusting step may be performed manually, in other embodiments the adjusting step may be performed automatically. In particular, the method may comprise treating a chronic total occlusion in a blood vessel.

Thus, the invention encompasses in one embodiment, a method of traversing an occlusion in a body lumen, comprising: (a) introducing into said body lumen having said occlusion a catheter comprising a spring element, a vibratable member, and a pulling member; wherein said spring element has proximal end and a distal end, said spring element attached at its proximal end to a distal end of said catheter and attached at its distal end to said vibratable member; and wherein said pulling member has proximal end and a distal end, said pulling member attached at its distal end to a distal component located at said distal end of said spring element, and operably connected at its proximal end to a vibrational energy source, said vibrational energy source capable of pulling and releasing said pulling member; (b) advancing said catheter until said vibratable member contacts a first face of said occlusion; (c) generating a series of pull and release units via said vibrational energy source sufficient to vibrate said vibratable member, wherein said series of pull and release units comprises at least one frequency and at least one amplitude; and (d) using said vibrations of said vibratable member to penetrate said first face of said occlusion. In another embodiment, the method further comprises: (e) stopping said vibration; (f) advancing said catheter to contact a new face of said occlusion; (g) repeating steps (a)-(d) until said new face of said occlusion is penetrated; and (h) repeating steps (a)-(g) until said occlusion is completely penetrated.

The method may further comprise the step of adjusting said at least one frequency and/or said at least one amplitude of vibration via a control unit based on occlusion hardness. In one aspect, said catheter includes a sensor and said occlusion hardness is determined from information from said sensor. In another embodiment the method further comprises the step of adjusting said at least one frequency and/or said at least one amplitude of vibration via a control unit based amplitude of vibration of said vibratable member. In one aspect, said catheter includes a sensor and said amplitude of vibration is determined from information from said sensor. In a further aspect of any of the above embodiments, said adjusting is done manually. In another further aspect of any of the above embodiments said adjusting is done automatically. In one aspect, said body lumen is a blood vessel.

As is evident by the descriptions above, the apparatus and system are compatible for use with guide wires, which are useful for guiding a catheter through a body lumen, in particular for guiding a catheter through a blood vessel. Stiff guide wires are used in the art for recanalizing blood vessel occlusion. In some cases, physicians prefer to use a stiff guide wire to penetrate a vascular occlusion but demand additional means to effect penetration where the occlusion is particularly difficult and perhaps safety is a concern. The apparatus and system of the invention provide that additional means; the apparatus and system of the invention are compatible with using a stiff guide wire in addition to the pull wire/spring element system to penetrate blood vessel occlusions, including total chronic occlusions. Accordingly, the invention encompasses a method of treating a chronic total occlusion in a body lumen by supplementing the method of penetrating an occlusion described above with using the tip of a guide wire to penetrate the occlusion. Thus, in one aspect of the method of treating an occlusion, said catheter includes a stiff guide wire, and said method further comprises advancing said stiff guide wire to penetrate said face of said occlusion alternately with steps (c)-(d). In another aspect, the method of treating an occlusion further comprises advancing said stiff guide wire to penetrate said face of said occlusion alternately with (c) generating a plurality of pulling and releasing cycles via said vibrational energy source sufficient to vibrate a vibratable member, wherein said plurality of pulling and releasing cycles comprises at least one frequency and at least one amplitude, and said vibratable member is located at a distal end of said spring element; and (d) using said vibrations of said vibratable member to penetrate said first face of said occlusion.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. An apparatus, comprising:
    a catheter, having a proximal end and a distal end;
    a spring element having a proximal end and a distal end, said proximal end of said spring element being affixed to said distal end of said catheter;
    a pulling member located within said catheter, said pulling member having a proximal end and a distal end, said distal end of said pulling member affixed to a distal component, thereby operably connected to said distal end of said spring element;
    a vibratable member; and
    a vibrational energy source located external of said catheter and operably connected to said proximal end of said pulling member, wherein said vibrational energy source is adapted to generate at least one oscillation in said vibratable member via said pulling member and said spring element by pulling and releasing said pulling member.

2. The apparatus of claim 1, wherein said pulling member is a flexible string.

3. The apparatus of claim 1, wherein said distal component is said vibratable member.

4. The apparatus of claim 1, wherein said distal component is said distal end of said spring element.

5. The apparatus of claim 1, wherein said vibratable member is a cap, and said cap is affixed to said distal end of said spring element.

6. The apparatus of claim 1, wherein said spring element is selected from the group consisting of: a compression spring, a helical spring, a leaf spring, a bellows, a compressible polymer, and an elastic membrane.

7. The apparatus of claim 1, wherein said vibrational energy source is selected from the group consisting of: an engine having a reciprocating member, a shaker, an actuator, and a solenoid.

8. The apparatus of claim 1, further comprising a catheter anchoring device.

9. The apparatus according to claim 8, wherein said catheter anchoring device is an expandable balloon.

10. A system, comprising:
    the apparatus of any one of claims 1-9; and
    a control unit adapted to control said vibrational energy source.

11. The system according to claim 10, wherein said oscillation comprises at least one frequency and at least one amplitude, and said at least one frequency and at least one amplitude are independently adjustable via said control unit.

12. The system according to claim 10, further comprising a sensor, and a processor functionally connected to said sensor and operably connected to said control unit, said processor being capable of analyzing input from said sensor.

13. The system according to claim 10, further comprising a tension adjustment mechanism to compensate for variations in pulling member path length when said catheter includes curvatures.

14. The apparatus of claim 1, wherein a frequency and amplitude of the generated vibrational energy is selected to be sufficient to penetrate an occlusion in a body lumen.

15. The apparatus of claim 1, wherein the at least one oscillation is an axial oscillation extending along a longitudinal axis of the vibratable member.

16. A method of traversing a vessel occlusion comprising:
    introducing into a vessel the apparatus of claim 1; and
    generating a series of pulling forces from said vibrational energy source upon said pulling member to oscillate said vibratable member.

17. The method of claim 16, further including:
    positioning said distal end of said catheter in contact with said occlusion; wherein said vibratable member is oscillated at an amplitude and frequency sufficient to penetrate said occlusion.

18. The method of claim 17, further including:
    advancing said apparatus through said occlusion as said vibratable member penetrates said occlusion.

19. The method of claim 16, wherein said vibratable member is oscillated at an amplitude and frequency sufficient to maneuver said catheter around obstacles in said vessel.

20. A method of improving deliverability of a catheter, comprising: introducing into a vessel having tortuous segments the apparatus of claim 1; and generating a series of pulling forces from said vibrational energy source upon said pulling member to oscillate said vibratable member at an amplitude and frequency sufficient to maneuver said catheter through said tortuous segments.

* * * * *